United States Patent
Kameneva et al.

(10) Patent No.: US 10,792,304 B1
(45) Date of Patent: Oct. 6, 2020

(54) HEMORHEOLOGIC APPROACH FOR REDUCTION/PREVENTION OF CANCER METASTASIS FORMATION

(71) Applicants: Marina V. Kameneva, Pittsburgh, PA (US); Denis Bragin, Albuquerque, NM (US); Edwin Nemoto, Albuquerque, NM (US); Richard Simmons, Pittsburgh, PA (US)

(72) Inventors: Marina V. Kameneva, Pittsburgh, PA (US); Denis Bragin, Albuquerque, NM (US); Edwin Nemoto, Albuquerque, NM (US); Richard Simmons, Pittsburgh, PA (US)

(73) Assignees: UNM Rainforest Innovations, Albuquerque, NM (US); University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 16/277,383

(22) Filed: Feb. 15, 2019

Related U.S. Application Data

(60) Provisional application No. 62/630,924, filed on Feb. 15, 2018.

(51) Int. Cl.
*A61K 31/765* (2006.01)
*A61P 35/04* (2006.01)

(52) U.S. Cl.
CPC .......... *A61K 31/765* (2013.01); *A61P 35/04* (2018.01)

(58) Field of Classification Search
None
See application file for complete search history.

(56) References Cited

U.S. PATENT DOCUMENTS

| | | | |
|---|---|---|---|
| 2003/0026855 A1* | 2/2003 | Kameneva | A61K 38/42 424/725 |
| 2007/0032451 A1* | 2/2007 | Thacker | A61K 31/728 514/54 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784. (Year: 1995).*
MedicineNet.com (http://www.medterms.com, 2004) (Year: 2004).*
Cancer Prevention, Mayo Clinic (2-16) https://www.mayoclinic.org/healthy-lifestyle/adult-health/in-depth/cancer-prevention/art-20044816 (Year: 2016).*
Lokeshwar et al. in Advances in Cancer Research 173, 35-65 (2014) (Year: 2014).*
Suefferlein et al. in European Oncology and Haematology 40-44 (2018) (Year: 2018).*
Bourguignon et al. disclose in Journal of Biological Chemistry 285(47), 36721-36735 (2010) (Year: 2010).*

* cited by examiner

*Primary Examiner* — Dennis Heyer
(74) *Attorney, Agent, or Firm* — Gonzales Patent Services; Ellen M. Gonzales

(57) ABSTRACT

Methods and compositions for the treatment, amelioration, or prevention of cancer and/or cancer metastasis by delivery of a hemodynamics altering agent such as a drag reducing polymer (DRP).

19 Claims, 7 Drawing Sheets

Fig. 17
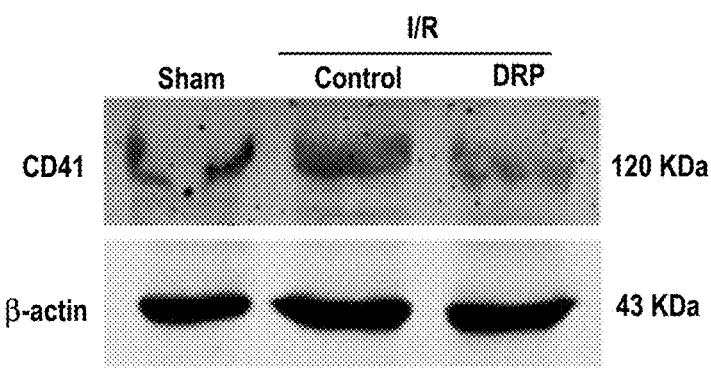
Fig. 18A  Fig. 18B  Fig. 18C
Sham    I/R      I/R
        Control  DRP
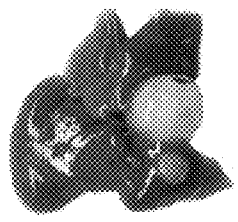 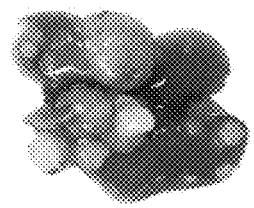 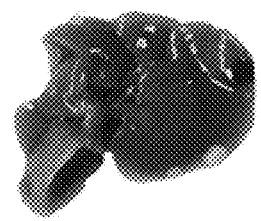
Fig. 19
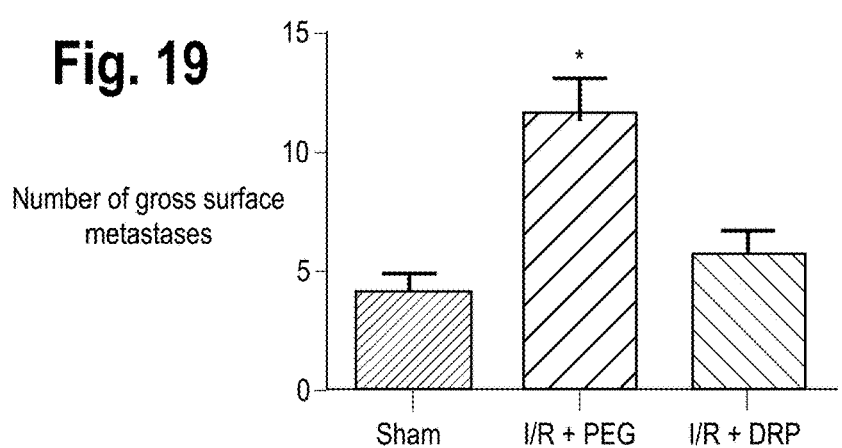

Sham

I/R / Control

I/R / DRP

HEMORHEOLOGIC APPROACH FOR REDUCTION/PREVENTION OF CANCER METASTASIS FORMATION

CROSS-REFERENCE TO RELATED APPLICATIONS

The following application claims benefit of U.S. Provisional Application No. 62/630,924, filed Feb. 15, 2018, which is hereby incorporated by reference in its entirety.

BACKGROUND

Cancer is the leading cause of death in the United States, accounting for 25% of all deaths, with approximately 1.7 million new cases being diagnosed each year and an annual economic burden of $125 billion. Metastases, a multi-step process of cancer cells spreading from primary site to different organs or tissues within the body, is responsible for about 90% of all cancer related deaths. However, clinically approved anticancer therapies generally target the primary tumor rather than metastatic processes, severely limiting the types and perhaps effectiveness of current therapies.

SUMMARY

According to an embodiment the present disclosure provides novel methods and compositions for treating cancer. According to various embodiments the present disclosure provides novel methods and compositions which prevent, inhibit or reduce the metastasis of cancer cells. According to various embodiments, the present disclosure provides for the treatment of a cancer patient by the delivery nanomolar concentrations of one or more blood-soluble polymers that positively modulate hemodynamics. According to a specific embodiment, the present disclosure provides for the treatment of a cancer patient by delivery of one or more polymers that modulate hemodynamics through rheological modification of the near-vessel-wall blood flow and at the vessel bifurcations. According to a more specific embodiment, the polymer is a drag-reducing polymer (DRP) or high molecular weight (i.e. close to or over $10^6$ Daltons) long-chain polymer soluble in fluids (water, saline, plasma, blood, etc.).

BRIEF DESCRIPTION OF THE DRAWINGS

FIG. 17 is a western blot showing CD41 and β-actin levels in sham, control, and DRP treated mice.

FIG. 18A is a representative photographic image of surface metastatic nodules in a liver from a sham mouse.

FIG. 18B is a representative photographic image of surface metastatic nodules in a liver from a control mouse three weeks after I/R.

FIG. 18C is a representative photographic image of surface metastatic nodules in a liver from a DRP-treated mouse three weeks after I/R.

FIG. 19 is a comparison of the number of gross metastasis seen in sham, control, and DRP-treated mice.

DETAILED DESCRIPTION

The metastatic cascades, a series of sequential events that must be completed in order for successful metastasis of the tumor cell, include: stromal invasion, intravasation into the systemic blood circulation, survival in the circulation, arrest in certain areas of the vasculature, and extravasation, followed by survival and proliferation at the ectopic site. Hemodynamics in microvasculature significantly affects the adhesion of circulating tumor cells to the vascular endothelial wall (via binding to neutrophils), and thereby subsequent extravasation. Given the importance of hemodynamic parameters in regulating cell-cell adhesion, alteration of microvascular hemodynamics is a potentially important but previously unexplored methodology for preventing extravasation of tumor cells and the subsequent development of metastases. Accordingly, the present disclosure provides a method of treating cancer wherein a composition capable of altering microvascular hemodynamics is delivered to a cancer patient so as to prevent, inhibit or reduce metastasis of cancer cells. This composition, may, for example, be a suitable polymer known or designed to alter microvascular hemodynamics.

Figure 1:
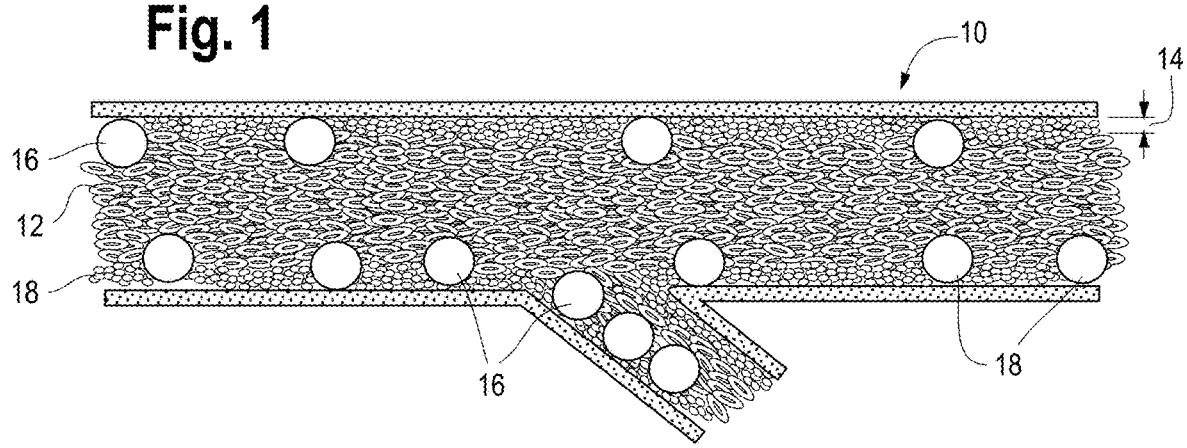
FIG. 1 is a schematic illustration of a typical microvessel and typical blood cell localization before (or without) DRP treatment.
Figure 2:
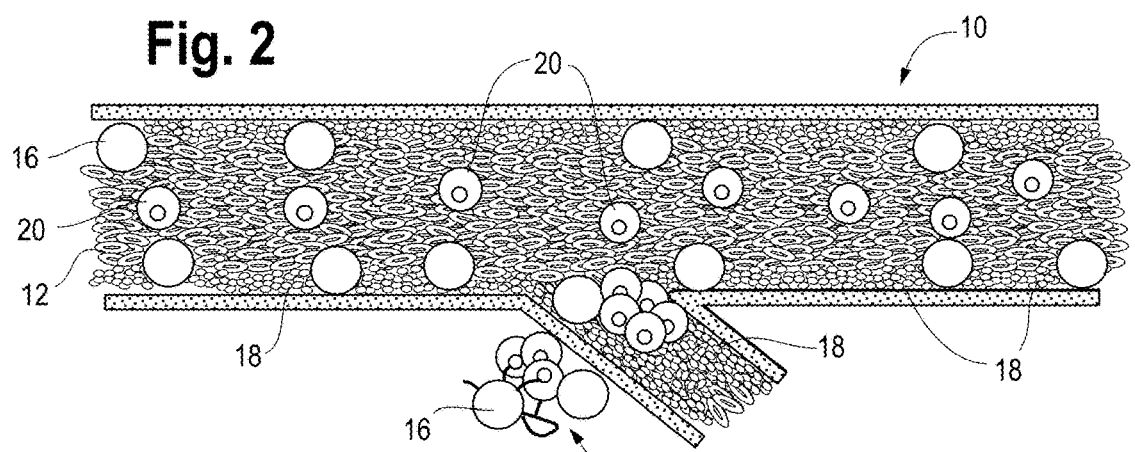
FIG. 2 is a schematic illustration of tumor cells within a microvessel without DRP treatment showing extravasation and metastatis of the tumor cells.

Local blood viscosity and velocity define near vessel wall hemodynamic parameters such as shear stress and shear rate. These parameters appear to have an effect on the transport of tumor cells modulating cell-cell collisions and cell-cell contact time. Specifically, a slow blood flow near the vessel wall increases the opportunity for circulating tumor cells to attach to neutrophils and vascular endothelial cells and extravasate blood vessels. Moreover, as shown in FIG. 1, red blood cells 12 tend to move towards the center of microvessels 10 (blood vessels having a diameter of less than approximately 300 micron) reducing the concentration of red blood cells (RBCs) near the vessel wall and resulting in the creation of a near-wall plasma layer 14 primarily comprising neutrophils 16 and platelets 18. As shown in FIG. 2, these phenomena result in an environment that is favorable for neutrophils 16 to both attach to circulating cancer cells 20 and transport them through the vessel wall, leading to metastasis 22.

Figure 3:
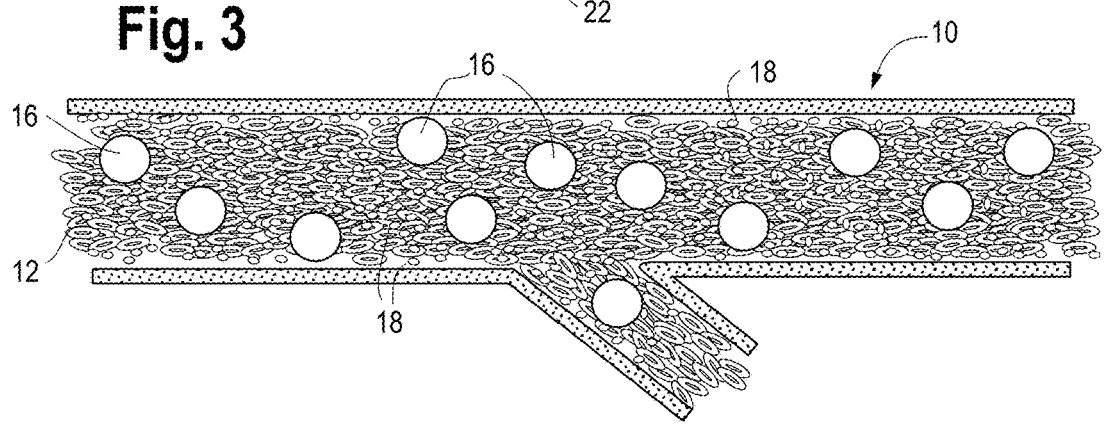
FIG. 3 is a schematic illustration of a typical microvessel and blood cell localization after DRP treatment.
Figure 4:
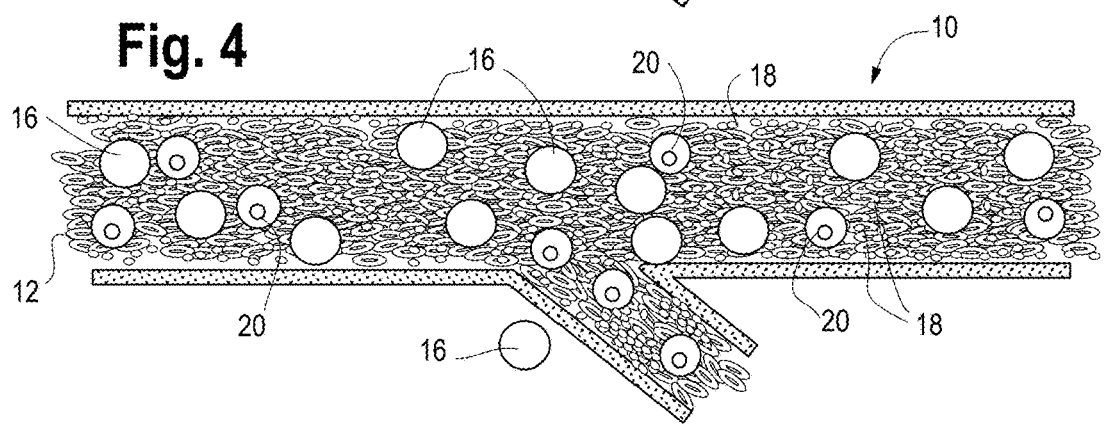
FIG. 4 is a schematic illustration of tumor cells within a microvessel after DRP treatment showing the lack of extravasation and metastatis.

In contrast, an alteration of hemodynamics by, for example, the introduction of a hemodynamic altering agent, results in increased blood flow and reduces platelet margination and leucocyte rolling near the vessel wall as shown in FIG. 3. This, in turn, reduces the interaction time during cell collisions, leading to a decrease in the opportunity for attachment between neutrophils and circulating tumor cells as shown in FIG. 4. Moreover, increased blood flow increases shear stress, which is known to impact surface expression of adhesion molecules in vascular endothelial cells. Accordingly, these phenomena are believed to lead to reduced opportunity for attachment, extravasation, and, ultimately, metastasis.

Accordingly, the present disclosure provides for the introduction of one or more compositions that reduce or eliminate cell-free layers near vessel walls, significantly increase the traffic of red blood cells in small vessels and capillaries, modulate the blood flow velocity profile, increase the near-wall velocity gradient, and/or increase shear forces to a patient in order to reduce the likelihood of tumor cells entering into vasculature from the primary site and metastasis of circulating tumor cells, producing a microvessel environment such as that shown in FIG. 3. According to some embodiments, the composition may take the form of a suitable polymer which is capable of achieving one or more of the above-described effects.

Figure 5:
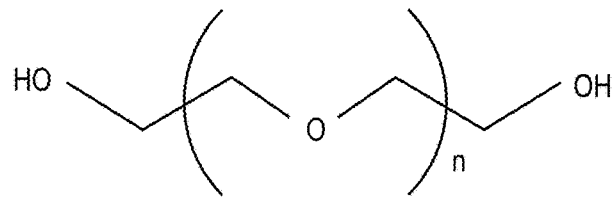
FIG. 5 is the chemical formula of Polyethylene oxides (PEO), an exemplary DRP.

In general, polymers suitable for use with the presently described methods include linear and branched long chain structure, blood soluble non-toxic macromolecules with a molecular weight close to or over $10^6$ Daltons, which are generally referred to the class of drag-reducing polymers (DRPs). Suitable DRPs exist as both naturally-occurring and synthetic polymers. Examples of naturally occurring DRPs include high molecular weight blood soluble non-toxic polysaccharides and polypeptides derived from plants such as okra, aloe vera and others, algae, gums, polypeptides and polysaccharides derived from bacteria, polymers derived from fish slimes, sea-water and fresh-water biological growths, ovomucin of egg-whites (see Grigorian S S, Kameneva M V, et al., Soviet Physics—Doklady 1980, 25, 10:815-816), biopolymers derived from human or animal blood (blood plasma and blood cells) (See, e.g., Grigorian S S, Kameneva M V, Smirnov V V, and Shakhnazarov A A. Method of extraction of drag reducing protein from blood. USSR Patent, #1341777, 1987). Specific examples include high molecular weight polyethylene oxide (the chemical formula of which is shown in FIG. 5) and hyaluronic acid. Non-natural synthetic polymers may be selected from a variety of water soluble synthetic high-molecular weight polymers such as high molecular weight polyethylene oxides, polyacrylamides, etc. As non-limiting examples, products with the following tradenames and available from the following companies may be useful: Polyethylene oxides (PEO) (Polyox water soluble resins WSR-301, and others, Union Carbide Co., USA) polyacrylamides (Praestol 2515TR, 2540TR and others, Stockhausen, Inc., Sweden), Carboxymethyl cellulose (Gum Technology Co.), gums such as Gum Guar (Sigma Chemical Co.), Tragacanth (Gum Technology Co.), Gum Karaya (Sigma Chemical Co.), Gum Xanthan (Sigma Chemical Co.).

Nanomolar concentrations of intravenous DRP significantly increase the traffic of red blood cells (RBC) in small vessels and capillaries specifically reducing or completely eliminating the cell free layer near the microvessel wall increasing wall shear stress. In addition, DRPs reduce flow separation and vortices at vascular bifurcations and significantly increase near-wall blood flow velocity, concentration of red blood cells, the number of functioning capillaries and microvascular flow volume. This enhancement of microvascular flow and red blood cell concentration increases oxygen delivery to hypoxic tissue and reduces ischemic injury as described, for example, in U.S. Pat. No. 9,763,975.

Accordingly, the present disclosure provides for the delivery of one or more types of DRPs to a subject who has been diagnosed with cancer or who is at increased risk for developing tumors as a result of cancer treatments such as, though not limited to, surgical resection or other procedures involving the removal of tumor cells including, but not limited to, liver ischemia-reperfusion, or who is at an increased risk for developing cancer, e.g., after exposure to known carcinogens, or after identification as being a carrier of a high-risk gene, etc. According to various embodiments the delivery of the DRP(s) could be in conjunction with or in lieu or other therapies. For example, the present disclosure contemplates the delivery of DRP(s) in conjunction with traditional cancer therapies including surgery, chemotherapy, radiation, hormonal therapy, immunotherapy, etc. Because DRPs are non-toxic, DRPs may be delivered when other cancer therapies are not advisable or even as a preventative measure.

Moreover, it should be noted that DRPs also have the effect of improving circulation in the tumor core, increasing oxygenation and thereby preventing necrotic tumor cell intravasation into the circulation as well as improving oxygenation in the core, thereby increasing sensitivity to radiation. Accordingly, it is contemplated that in some cases it may be desirable to treat a patient who is undergoing radiation treatment with the herein described DRP-based therapies.

According to some embodiments, the polymers described herein may be modified to increase their efficacy as biologicals. For example, the polymers could be modified to increase water solubility and/or stability.

According to various embodiments, the DRPs are delivered in nanomolar concentrations. According to various embodiments, the DRPs are delivered in such a way that a desired final blood concentration is achieved. According to some embodiments the desired final blood concentration is between 0.1 and 5 (μg/ml). The DRP may be formulated as a sterile solution in an appropriate pharmaceutical buffer or carrier. Examples of suitable buffers include, but are not limited to, normal saline, phosphate buffer saline (PBS) or any other physiological saline.

Delivery can be given intravenously as a single dose, multiple separate doses, or via a constant delivery mechanism (i.e. an infusion pump). According to various embodiments, the dose(s) may be delivered via a single injection, repetitive injection, or continuous dripping or infusion. According to a further embodiment the present disclosure provides a constant delivery mechanism designed to maintain a desired DRP concentration (e.g. between 0.1 and 5 ppm) in the subject's blood for an extended or even indefinite period of time. According to various embodiments, this extended period of time could be multiple hours, days, weeks, months, or even years. For example, PEO molecules are mechanically degraded in the vascular system into shorter fragments which are then excreted by the urinary system, with a mean retention time of approximately 77 hours. Accordingly, if PEO is used as the DRP, it may be desirable to deliver the PEO to the patient every ~72 hours, or 2-3 times per week in order to maintain an effective concentration of the high molecular weight PEO in the patient's system.

According to some embodiments, this constant delivery mechanism could be configured to monitor blood flow velocity (via, for example, an integrated Doppler) and/or DRP concentration and deliver an appropriate constant or variable dosage of DRP to maintain a desired blood flow velocity and/or DRP concentration. In this configuration it will be understood that the "constant delivery mechanism" may not, in fact, deliver a constant dosage of DRP to the target subject, but rather would be configured to deliver an appropriate dosage when and as needed. It should be understood that other, non-intravenous delivery options may also be used oral, rectal, intraperitoneal, and transcutaneous methods.

While the Examples below are primarily directed to two specific types of solid cancer, breast cancer and liver cancer, and, one hematologic (liquid) cancer, namely leukemia, it will be understood that the presently described methods and compositions are suitable for use in a wide range of solid and hematologic cancer therapies, prevention, etc.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

EXAMPLES

Inhibition of Metastasis of Human Breast Cancer Cells

A DRP solution was produced by dissolving polyethylene oxide (PEO [4000 kDa MW]-Sigma-Aldrich, St. Louis, Mo., USA) in sterile saline at a concentration of 0.1%. The solution was dialyzed against saline for 24 hours using a 50-kDa MW cut-off membrane (regenerated cellulose membrane; Spectra/Por Spectrum Laboratories, Inc., Rancho Dominguez, Calif., USA) to remove low molecular weight fractions. The PEO solution was finally diluted with saline to a concentration of 50 ppm and sterilized using a 0.22-um filter.

MDA-MB-231 (MDA-231) breast cancer cell lines (ATCC, Menassas, Va., USA) stabling expressing red fluorescence protein (RFP) were generated and cultured as described in Gau et al., Fluorescence resonance energy transfer (FRET)-based detection of profilin-VASP interaction *Cell Mol Bioeng.* 2011; 4(1):1-8.

Female athymic nude mice (~25 g weight) were injected with either the DRP solution (DRP-treated mice) or sterile saline (control mice) and then subsequently with the RFP expressing MDA-231 breast cancer cells. In some experiments, two additional rounds of DRP or sterile saline injections were performed prior to sacrificing the animals. FITC-lectin was injected 30 minutes prior to sacrificing the animals.

Comparisons of the DRP treated and control mice 2 hours after the initial MDA-231 injection, shows similar patterns in both populations. As expected, the MDA-231 cells were still restricted to the lung microvasculature. Specifically, the MDA-231 cells mimicking the honeycomb network of the lung vasculature at the 2 hour mark. The lungs from the DRP treated mice were nearly identical. However, a stark contrast could be seen at the 24-hour time point. Specifically, the lung microvasculature of the control animals showed very little presence of MDA-231, and extravasated tumor cells can be seen in the lung parenchyma of the control animals. The lungs of DRP treated mice at 24 hours were strikingly similar to the lungs of the control mice at 2 hours. Specifically, the MDA-231 cells were retained in the microvasculature of the DRP treated mice. Moreover, the MDA-231 cells in the DRP treated mice did not appear to have extravasated to the lung parenchyma. See also, Ding et al., "Nanomolar concentration of blood-soluble drag-reducing polymers inhibits experimental metastasis of human breast cancer cells" Breast Cancer—Targets and Therapy 2017:9 61-65, which is hereby incorporated by reference for all purposes.

Figure 6:
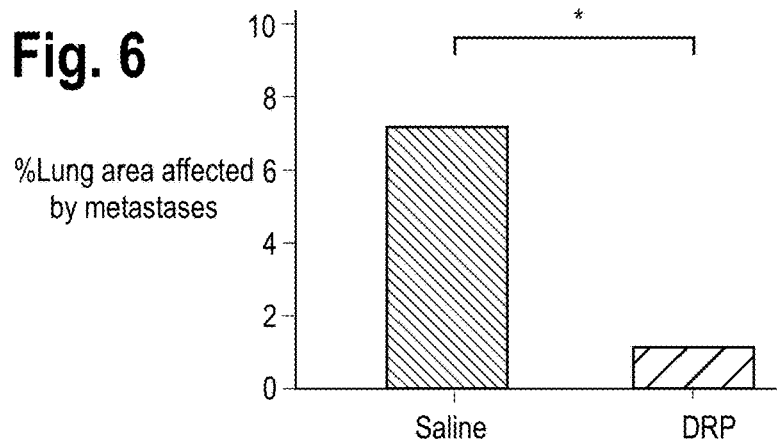
FIG. 6 is a bar graph showing a comparison of the average percent of lung area affected by metastases between control and DRP-treated mice.

Longer term studies of lung colonization of breast cancer cells 10-11 days after injection resulted in control animals developing prominent lung metastases, while DRP treated mice showed the presence of only a few individual and tiny clusters of tumor cells. FIG. 6 is a bar graph comparing the average percentage of lung area affected by metastases between the two populations. The data was based on analyses of 20 random 10× lung fields pooled from three mice in each group. See also, Ding et al., incorporated by reference above.

Decrease in Hepatic Injury and Metastasis after Liver-Ischemia Reperfusion

DRP (Polyethylene oxide (PEO), 4 million Da MW, Sigma-Aldrich) was given to animals intraperitoneally at various concentrations. Each polymer preparation was tested or drag reducing and rheological properties as described in Kameneva et al., "Blood soluble drag-reducing polymers prevent lethality from hemorrhagic shock in acute animal experiments." Biorheology, 2004; 41: 53-64, which is hereby incorporated by reference in its entirety for all purposes. Control animals were treated with the same chemical but with significantly lower MW (PEG, polyethylene glycol, 1000 Da MW, Sigma-Aldrich), which does not have drag-reducing properties.

A nonlethal model of segmental (70%) hepatic warm ischemia and reperfusion was used to produce the liver ischemia-reperfusion model. See, e.g., Kameneva, "Microrhelogical effects of drag-reducing polymers in vitro and in vivo." International Journal of Engineering Science. 2012; 59: 168-83; and Tsung et al., "The transcription factor interferon regulatory factor-1 mediates liver damage during ischemia-reperfusion injury." AmJPhysiol GastrointestLiver Physiol. 2006; 290:G1261-G8. DRP (100 ul, concentrations 10 to 1000 ppm per mouse) or PEG (100 ul, 1000 ppm) were injected intraperitoneally immediately after ischemia. Sham animals underwent anesthesia, laparotomy, and exposure of the portal triad without hepatic ischemia.

The first set of metastases experiments were designed to evaluate whether I/R increased tumor growth in a model of circulating micrometastases. Colorectal liver metastases were induced in mice as described Tohme et al., "Neutrophil Extracellular Traps Promote the Development and Progression of Liver Metastases after Surgical Stress." Cancer Res. 2016. doi: 10.1158/0008-5472.CAN-15-1591. In brief, at the time of reperfusion $5 \times 10^4$ MC38 cells (colorectal cancer cell lines) were injected into the spleen using a 27-gauge needle. At the same time, mice received either DRP or PEG intraperitoneally. Tumor cells were allowed to circulate for 10 minutes before splenectomy. The next set of experiments was designed to evaluate whether DRP protects from I/R-induced increased growth of already established micrometastatic disease. In these experiments, tumor cells were injected into the spleen through a small left lateral flank incision followed by splenectomy. Micrometastases were allowed to develop throughout the liver for 5 days. Then the mice underwent either hepatic I/R with DRP or PEG injection as described above.

Figure 7:
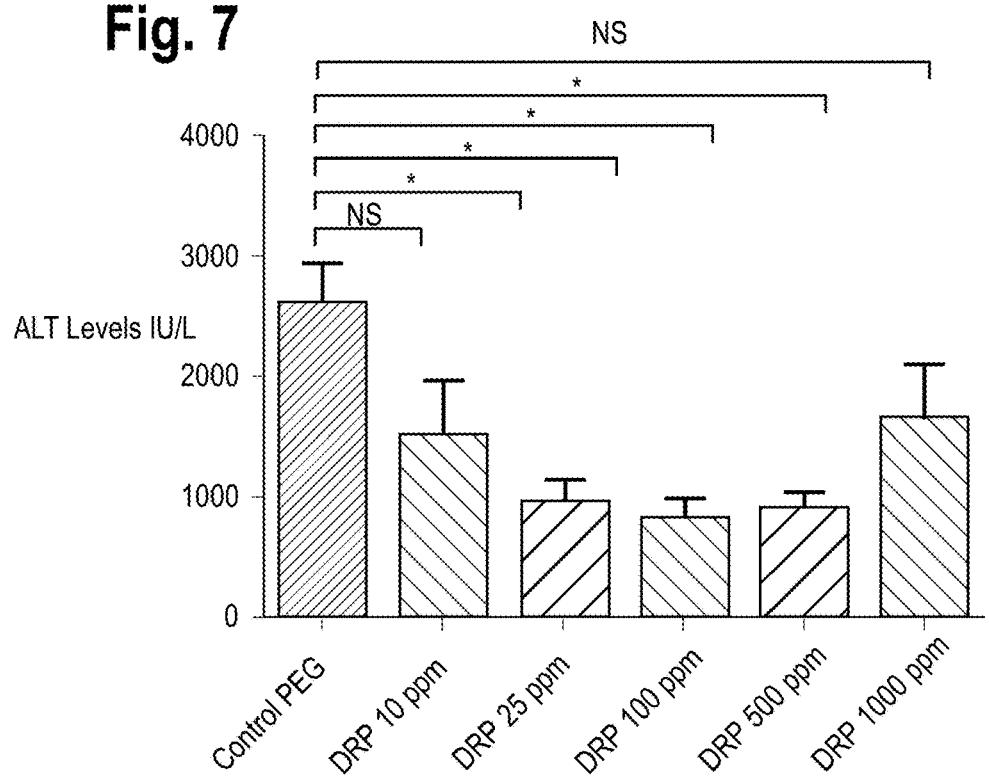
FIG. 7 is a bar graph showing a comparison of I/R treated mice that were given different concentrations of DRPs or control PEG intraperitoneally at the time of reperfusion. Serum ALT levels were assessed after 1 hour of ischemia and 6 hours of reperfusion. Data represent the mean+/−SE (n=6 mice/group).
Figure 8:
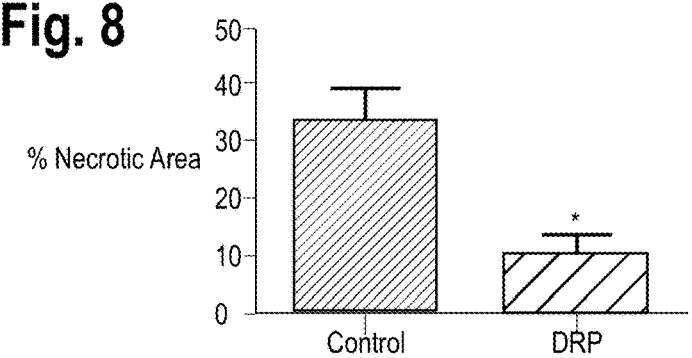
FIG. 8 is a bar graph showing quantification of necrotic hepatocytes in H&E stained liver sections from control or DRP-treated mice 6 hours after reperfusion.
Figure 9:
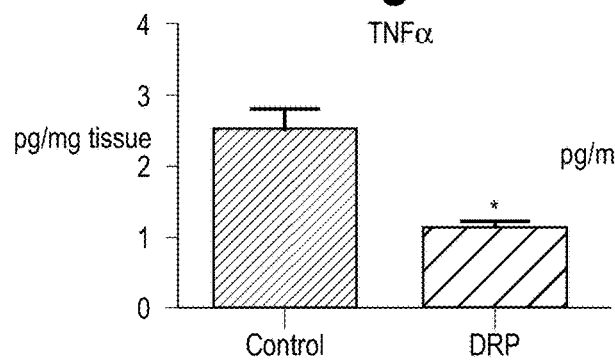
FIG. 9 is a bar graph comparing I/R-induced inflammatory levels of TNF-α in control or DRP treated mice 6 hours after reperfusion.
Figure 10:
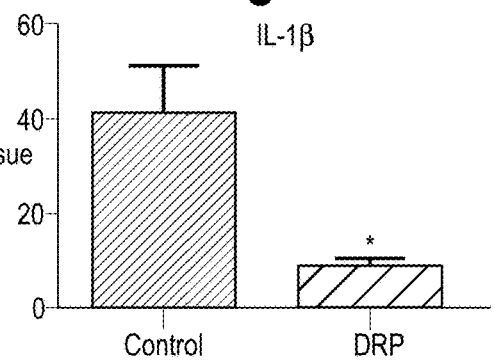
FIG. 10 is a bar graph comparing I/R-induced inflammatory levels of IL-1β in control or DRP treated mice 6 hours after reperfusion.
Figure 11:
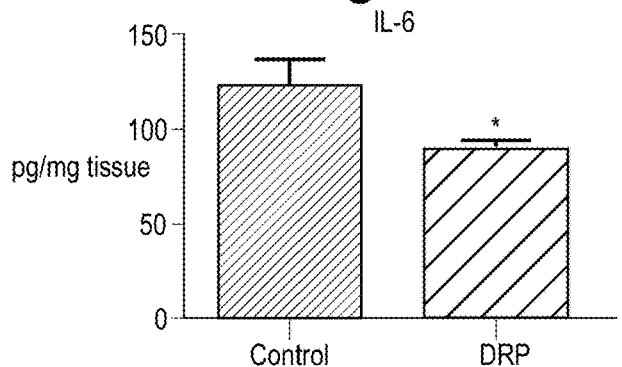
FIG. 11 is a bar graph comparing I/R-induced inflammatory levels of IL-6 in control or DRP treated mice 6 hours after reperfusion.

Turning to FIG. 7, it can be seen that administration of DRPs significantly reduced liver damage 6 hours after reperfusion, as evidenced by reduced serum ALT levels compared with mice receiving PEG in doses as low as 25 ppm and as high as 500 ppm. ALT levels were not significantly reduced at 1000 ppm. Accordingly, a DRP concentration of 100 ppm was used for the rest of the experiments, as it provoked the least amount of ALT release after I/R without visible effect on the mice. The intraperitoneal route was chosen to allow more gradual and prolonged direct access to the venous circulation via the diaphragmatic lymphatics without prolonging anesthesia needed for slow intravenous infusion of the viscoelastic DRPs. Histology was consistent with the serum ALT levels of liver damage, with the presence of severe sinusoidal dilatation and confluent pericentral hepatocellular necrosis in liver tissue from control mice but not from DRP treated mice. The bar graph in FIG. 8 shows the quantification of necrotic hepacytes in H&E stained liver sections from control or DRP-treated mice 6 hours after reperfusion. In addition, the liver tissue levels of the proinflammatory cytokines, TNFα, IL-1β and IL-6 were significantly lower in recipients of DRPs compared with control mice subjected to liver I/R (FIGS. 9, 10, and 11, respectively). See also, Tohme et al., "Drag reducing polymers decrease hepatic injury and metastases after liver ischemia-reperfusion" Oncotarget, 2017, Vol. 8, (No. 35), 59854-59866, which is hereby incorporated by reference in its entirety for all purposes.

Figure 12:
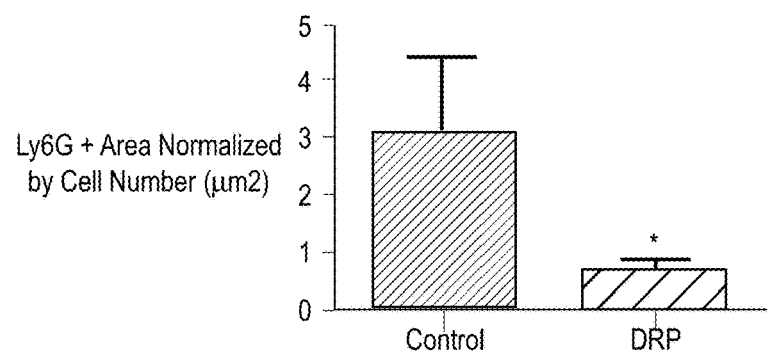
FIG. 12 is a bar graph comparing infiltration of neutrophils in DRP treated vs control mice 6 hours after reperfusion.
Figure 13:
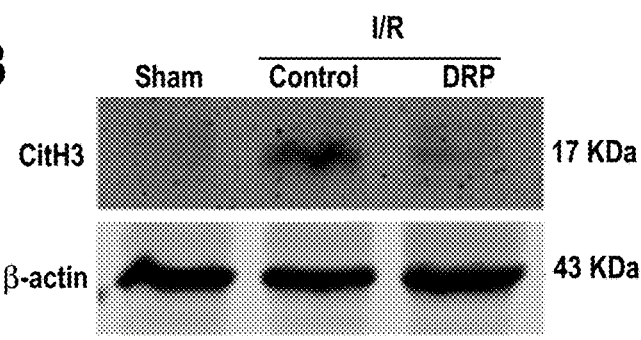
FIG. 13 is a Western Blot of Cit-H3 protein levels in sham, I/R+control PEG, and I/R_DRP mice groups 6 hours after reperfusion.
Figure 14:
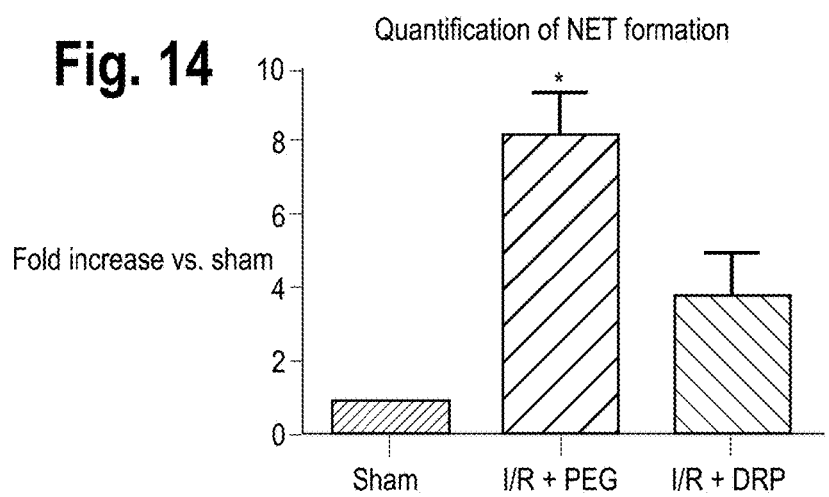
FIG. 14 is a bar graph comparing NETs formation in liver tissue 6 hours after reperfusion as assessed by serum levels of MPO-DNA. Results are expressed as the relative folds increase of MPO-DNA levels compared with sham; mean+/−SEM (n=6/group). *P<0.05.

Analysis by confocal microscopy showed that there was a significant decrease in infiltrating neutrophils within the ischemic liver lobes 6 hours after mice were subjected to I/R in the mice treated with DRPs compared to liver lobes from mice treated with PEG. (The confocal microscopy data is quantified in the bar graph shown in FIG. 12) As shown in the Western blot in FIG. 13, ischemic lobes also exhibited significantly higher levels of citrullinated-histone H3 (Cit-H3), a specific marker of NET formation, after liver I/R which was significantly reduced when mice were treated with DRPs. Furthermore, as shown in FIG. 14, the serum level of MPO-DNA complexes, a marker that circulating nucleosomes are derived from NET formation, was significantly decreased in mice undergoing liver I/R with DRP treatment compared to controls. See also, Tohme et al., incorporated by reference above.

Figure 15:
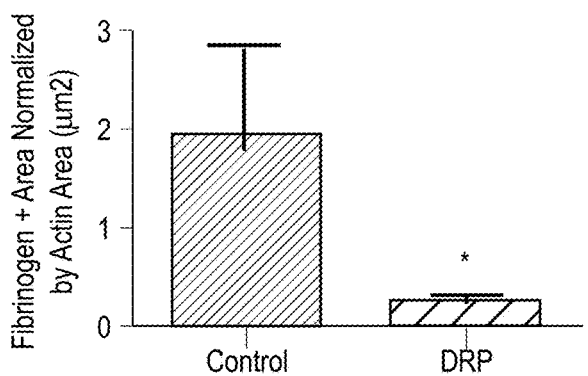
FIG. 15 is a bar graph comparing fibrinogen levels in DRP treated vs control mice.
Figure 16:
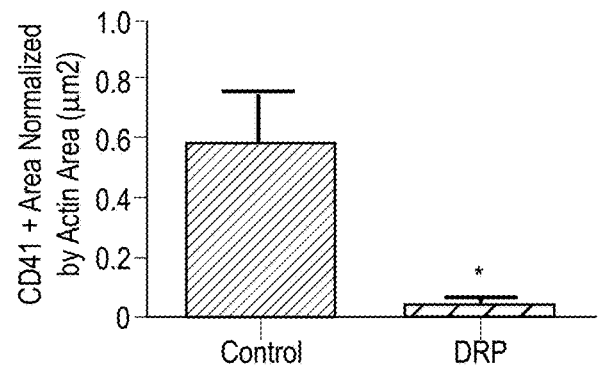
FIG. 16 is a bar graph comparing CD41 levels in DRP treated vs control mice.

Examination of liver sections of hepatic lobes 6 hours after I/R demonstrated a significant increase in platelet aggregation within liver sinusoids and a significant increase in fibrin-rich microthrombi formation in mice treated with control PEG compared to DRPs. (FIGS. 15 and 16.) In similar findings, DRPs significantly decreased platelet sequestration within the hepatic lobes exposed to I/R as seen on Western Blots examining the expression of CD41, a platelet marker (FIG. 17). See also, Tohme et al., incorporated by reference above.

Experiments aimed at mimicking the surgical setting for major resection of livers in cancer patients were performed. In general, MC38 cells were injected into the spleen immediately after a 60-minute period of lobar I/R. Recipients of tumor cells and cohort controls were given DRPs or PEG, respectively, at the time of reperfusion and tumor injection. Quantification of gross hepatic metastases was performed when the mice were sacrificed at 3 weeks. FIGS. 18A-C shows that livers of mice subjected to I/R without DRPs treatment contained significantly more hepatic metastases compared with mice not receiving I/R (mean 13 nodules in I/R versus 2 nodules in sham; p<0.001). Administration of DRPs after liver I/R resulted in a 69% reduction in tumor nodules compared with untreated I/R mice at 3 weeks (mean 4 nodules, p=0.003) (FIG. 19). See also, Tohme et al., incorporated by reference above.

Figure 20A:
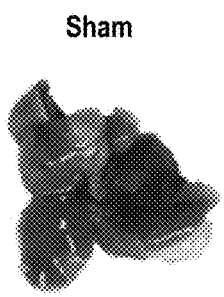
FIG. 20A is a photographic image of hepatic nodules a representative liver from a sham mouse.
Figure 20B:
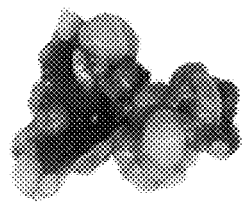
FIG. 20B is a photographic image of hepatic nodules a representative liver from a control mouse three weeks after I/R.
Figure 20C:
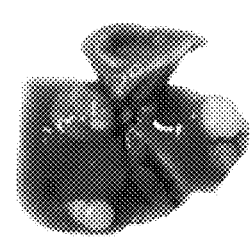
FIG. 20C is a photographic image of hepatic nodules a representative liver from a DRP-treated mouse three weeks after I/R.
Figure 21:
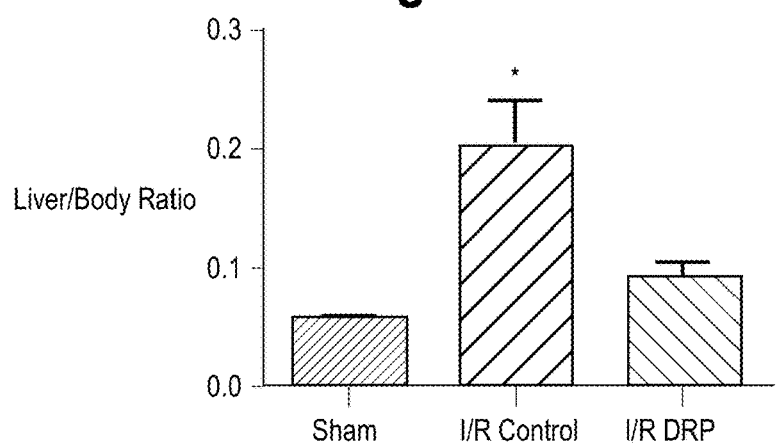
FIG. 21 is bar graph comparing the live/body ratio of hepatic nodules in sham, I/R control and I/R DRP-treated mice three weeks after I/R.
Figure 22:
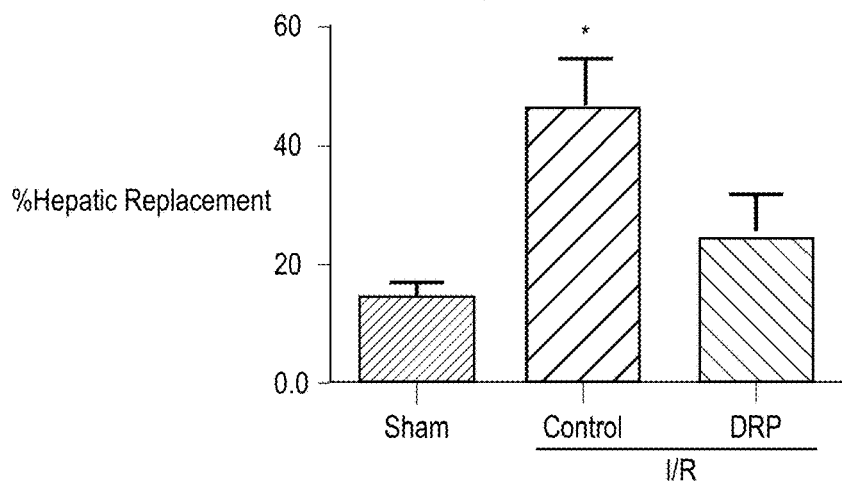
FIG. 22 is a bar graph comparing the percentage of hepatic replacement by metastatic tumor in sham, I/R control and I/R DRP-treated mice three weeks after I/R.

Experiments examining whether DRPs can affect the growth of existing micrometastases were also performed. In general, MC38 cells were injected into the spleen and micrometastases were allowed to develop. Five days later, the mice were subjected to I/R surgery and treated with PEG (as a control) or with DRPs. Mice treated with DRP displayed significantly decreased tumor growth, which was grossly appreciable as smaller and less numerous tumors (FIGS. 20A-C). In addition, DRP significantly decreased the tumor load after I/R as evidenced by the liver-to-body weight ratio and the tumor hepatic replacement area (FIGS. 21-22). Tumors from mice treated with DRP after I/R showed a significant decrease in proliferation compared to PEG-treated mice subjected to I/R as evident by decreased Ki6 staining. See also, Tohme et al., incorporated by reference above.

Decrease in Metastasis of Leukemia Cells

In this study, a xenograft model of human B cell precursor (BCP)-ALL in immunocompromised mice was employed. The bi-weekly injections were started at 5 days after leukemia cells injection, followed by liver harvesting for Flow Cytometry at day 20.

Figure 23:
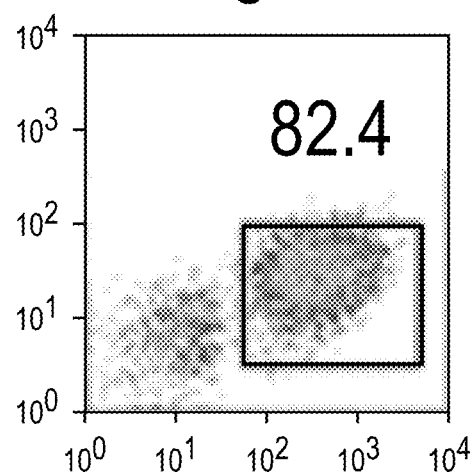
FIG. 23 show the metastasis of leukemia cells in the livers of mice treated with saline.
Figure 24:
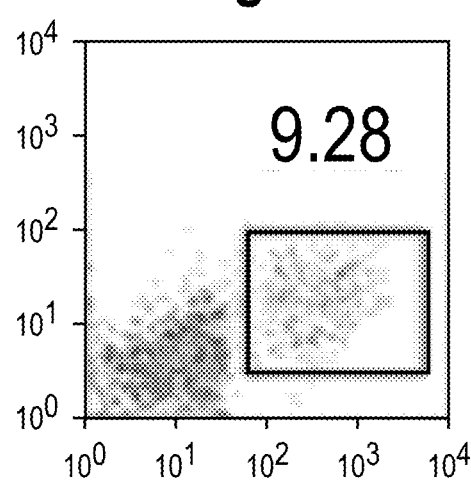
FIG. 24 show the metastasis of leukemia cells in the livers of mice treated with DRP.

FIGS. 23 and 24 show the metastasis of leukemia cells in the livers of mice treated with saline (FIG. 23) and DRP (FIG. 24) showing near 10 times reduction of metastasis in DRP mice.

What is claimed is:

1. A method for treating or ameliorating, cancer metastases in a subject having breast cancer comprising delivery to the subject a dosage of polyethylene oxide (PEO) wherein the PEO is a drag reducing polymer (DRP) that is a linear or branched blood soluble non-toxic macromolecule with a molecular weight near or over $10^6$ Daltons.

2. The method of claim 1 wherein the PEO is delivered to the subject before, during, or after an event known or believed to increase the likelihood of the presence of cancer cells in the subject's microvasculature.

3. The method of claim 2 wherein the PEO is delivered to the subject before, during, or after surgery.

4. The method of claim 1 wherein multiple dosages are delivered to the subject in order to maintain a specific concentration or concentration range in the subject's blood for an extended period of time.

5. The method of claim 4 wherein the extended period of time is longer than 72 hours.

6. The method of claim 4 wherein the extended period of time is longer than one week.

7. The method of claim 4 wherein the extended period of time is longer than one month.

8. The method of claim 1 wherein the dosage of PEO produces an intravenous concentration of PEO in the subject's blood of between 0.1 and 10 ppm.

9. The method of claim 1 wherein the dosage of PEO produces an intraperitoneal concentration of PEO between 10 and 100 ppm.

10. The method of claim 5 wherein multiple dosages are delivered to the subject in order to maintain an intravenous concentration of between 0.1 and 10 ppm over an extended period of time.

11. The method of claim 1 wherein the PEO is delivered in conjunction with another method of treatment.

12. The method of claim 11 wherein the other method of treatment is radiation therapy.

13. The method of claim 1 wherein the subject has developed detectable cancer-related tumors.

14. The method of claim 1 wherein the PEO has a molecular weight of 4000 kDa+/−3500 kDa.

15. A method for the reduction and/or prevention of cancer metastasis by rheological modulation of blood flow to reduce and/or prevent extravasation of cancer cells comprising delivering a dosage of polyethylene oxide (PEO) wherein the PEO is a linear or branched, blood soluble non-toxic macromolecule with a molecular weight over $10^6$ Daltons.

16. The method of claim 15 wherein multiple dosages are delivered.

17. The method of claim 16 wherein the dosage is delivered after surgery.

18. The method of claim 15 wherein the surgery comprises removal of cancer cells.

19. The method of claim 15 wherein the PEO has a molecular weight of 4000 kDa+/−3500 kDa.

* * * * *